US010196367B2

(12) United States Patent
Kim et al.

(10) Patent No.: US 10,196,367 B2
(45) Date of Patent: Feb. 5, 2019

(54) BLEED-OUT PREVENTING AGENT, COMPOSITION FOR PREVENTING BLEED-OUT INCLUDING THE SAME, AND METHOD OF PREVENTING BLEED-OUT

(71) Applicant: HAESUNG DS CO., LTD, Changwon-si (KR)

(72) Inventors: Soeng Ick Kim, Changwon-si (KR); Dong-Soo Shin, Changwon-si (KR)

(73) Assignee: HAESUNG DS CO., LTD, Changwon-si (KR)

(*) Notice: Subject to any disclaimer, the term of this patent is extended or adjusted under 35 U.S.C. 154(b) by 497 days.

(21) Appl. No.: 14/645,904

(22) Filed: Mar. 12, 2015

(65) Prior Publication Data
US 2015/0266835 A1   Sep. 24, 2015

(30) Foreign Application Priority Data
Mar. 18, 2014   (KR) .................. 10-2014-0031816

(51) Int. Cl.
  *C07D 251/46*   (2006.01)
  *H01L 23/29*   (2006.01)
  *A61K 31/53*   (2006.01)
  *H01L 23/00*   (2006.01)

(52) U.S. Cl.
  CPC ............ *C07D 251/46* (2013.01); *A61K 31/53* (2013.01); *H01L 24/97* (2013.01)

(58) Field of Classification Search
  CPC .. C07D 251/46; C07D 251/18; C07D 251/20; C07D 251/24; C07D 251/30; C07D 251/38; C07D 251/40; C07D 251/42; C07D 251/48; C07D 251/52; C07D 251/54; A61K 31/53
  USPC ....... 544/194, 220, 195, 198, 205, 207, 209, 544/210, 212, 214, 219, 221, 223, 213; 514/245
  See application file for complete search history.

(56) References Cited

U.S. PATENT DOCUMENTS

| | | | | | |
|---|---|---|---|---|---|
| 2,375,733 | A | * | 5/1945 | Kaiser | C07D 251/46 544/210 |
| 2,634,270 | A | * | 4/1953 | Nielsen | C07F 9/65215 544/195 |
| 2,991,285 | A | * | 7/1961 | Feely | C07D 213/803 546/145 |
| 2,996,505 | A | * | 8/1961 | Schwarze | C07D 251/38 126/104 R |
| 3,093,645 | A | * | 6/1963 | Shaw | D06M 13/358 544/181 |
| 3,210,350 | A | * | 10/1965 | D Alelio | C07F 9/65216 252/390 |
| 3,305,390 | A | * | 2/1967 | Shaw | D06M 13/358 427/389.9 |
| 3,654,274 | A | * | 4/1972 | Chance | C07F 9/65216 106/18.16 |
| 3,787,376 | A | * | 1/1974 | Nakamura | C08K 5/378 525/401 |
| 3,855,220 | A | * | 12/1974 | Fischer | C07D 213/78 544/180 |
| 4,038,197 | A | * | 7/1977 | Caspari | C07D 251/46 508/257 |
| 4,977,262 | A | * | 12/1990 | Herzlinger | C07D 251/34 106/18.21 |
| 5,240,826 | A | * | 8/1993 | Miyasaka | G03C 1/09 430/445 |
| 5,288,868 | A | * | 2/1994 | Reinehr | C07D 251/22 544/219 |
| 5,304,646 | A | * | 4/1994 | Cipolli | C07D 251/52 544/113 |
| 5,350,848 | A | * | 9/1994 | Cipolli | C07F 9/65216 544/113 |
| 5,534,573 | A | * | 7/1996 | Leake | C07F 9/65216 523/451 |
| 6,011,135 | A | * | 1/2000 | Mori | C07D 251/46 528/373 |
| 6,150,362 | A | * | 11/2000 | Henkin | C07D 251/18 514/245 |
| 7,208,597 | B2 | * | 4/2007 | Holzl | A01N 43/66 252/301.23 |

FOREIGN PATENT DOCUMENTS

| | | | | |
|---|---|---|---|---|
| EP | 0957096 A1 | * | 11/1999 | ........... C07D 251/20 |
| KR | 2000-0069912 A | | 11/2000 | |
| KR | 10-2007-0110892 A | | 11/2007 | |
| KR | 10-2009-0009201 A | | 1/2009 | |
| WO | 2011074496 A1 | | 6/2011 | |

OTHER PUBLICATIONS

Kim et al. Kobunshi Ronbunshu (1999), 56(5), 314-322; CA 131:130558,1999, CAPLUS Abstract provided.*
Mori et al. JP 11291259, Oct. 26, 1999; CA 131:300386,1999, CAPLUS Abstract provided.*
Pccompound-List-1, Selected items 1-5, Create Date Mar. 26, 2005 to Dec. 5, 2007.*
JP 2004009340,Jan. 15, 2004; Machine Translation.*
JP 2004009340,Jan. 15, 2004; CA 140, 80312, 2004. CAPLUS Abstract.*
Pccompound 1-14,Create Date Mar. 26, 2005 to Create Date Nov. 5, 2014.*
Pccompound 1-3,Create Date Mar. 27, 2005 to Create Date Jun. 21, 2011.*

* cited by examiner

*Primary Examiner* — Venkataraman Balasubramanian
(74) *Attorney, Agent, or Firm* — Sughrue Mion, PLLC (57) ABSTRACT

Provided are a bleed-out preventing agent and a composition for preventing bleed-out including the same.

6 Claims, 4 Drawing Sheets

BLEED-OUT PREVENTING AGENT, COMPOSITION FOR PREVENTING BLEED-OUT INCLUDING THE SAME, AND METHOD OF PREVENTING BLEED-OUT

RELATED APPLICATIONS

This application claims the benefit of Korean Patent Application No. 10-2014-0031816, filed on Mar. 18, 2014, in the Korean Intellectual Property Office, the disclosure of which is incorporated herein in its entirety by reference.

BACKGROUND

1. Field

One or more embodiments of the present invention relate to bleed-out preventing agents, compositions for preventing bleed-out including the same, and methods of preventing bleed-out.

2. Description of the Related Art

Lead frames for packaging semiconductors or printed circuit boards may be subjected to an assembly process in which semiconductor chips and external circuits are connected to form a single semiconductor package, and a die bonding process, a wire bonding process, and a molding process are generally included in the assembly process.

A die bonding process is a process in which a die pad such as a lead frame or printed circuit board and a semiconductor chip are fixed with an adhesive, wherein a die bonding resin (e.g., an epoxy-based resin) is mainly used as the adhesive.

A bleed-out phenomenon may occur in which resins or additives are leached out according to the presence of surface contamination due to organics such as a discoloration inhibitor and a sealing agent, a degree of surface roughness due to plating of a die pad, or physical properties of a die bonding resin used. Bleed-out may decrease die-bonding strength or may cause defects in the subsequent wire bonding process. Also, the bleed-out may cause reliability degradation of a finished semiconductor package.

In a case where a surface of a die pad is coated with silver, $Ag_2S$ may be formed on the silver-plated surface of the die pad due to sulfur and oxygen in air to cause discoloration. Thus, this may not only decrease the appearance quality of a product, but may also cause defects in a wire bonding process. In a case where the surface of the die pad is not plated with a noble metal such as gold, silver, and palladium, copper in the die pad may be in contact with oxygen in air to cause surface oxidation. Thus, this may not only decrease the appearance quality of a product, but may also cause defects in a soldering process.

SUMMARY

One or more aspects according to embodiments of the present invention are directed toward bleed-out preventing agents, compositions for preventing bleed-out including the same, and methods of preventing bleed-out.

Additional aspects are set forth in part in the description which follows and, in part, will be apparent from the description, or may be learned by practice of the presented embodiments.

According to one or more embodiments of the present invention, a bleed-out preventing agent is represented by Formula 1:

$$(R_1)_{a1}-X-(R_2)_{a2} \quad \text{<Formula 1>}$$

In Formula 1, X is selected from the group consisting of a $C_6$-$C_{60}$ arylene group and a $C_1$-$C_{60}$ heteroarylene group;

$R_1$ is selected from the group consisting of a $C_1$-$C_{60}$ alkyl group, a fluorine-substituted $C_1$-$C_{60}$ alkyl group, a $C_6$-$C_{60}$ aryl group, a fluorine-substituted $C_6$-$C_{60}$ aryl group, —NH($Q_1$), and —N($Q_1$)($Q_2$); and $Q_1$ and $Q_2$ are each independently selected from the group consisting of a $C_1$-$C_{60}$ alkyl group, a fluorine-substituted $C_1$-$C_{60}$ alkyl group, a $C_6$-$C_{60}$ aryl group, and a fluorine-substituted $C_6$-$C_{60}$ aryl group;

a1 is selected from 1, 2, and 3;

$R_2$ is selected from functional groups including one or more heterogeneous elements that are selected from the group consisting of oxygen (O), sulfur (S), boron (B), nitrogen (N), phosphorous (P), and silicon (Si); and a2 is selected from 1, 2, and 3.

In Formula 1, X may be selected from the group consisting of a phenylene group, a naphthylenylene group, a phenanthrenylene group, an anthracenylene group, a triphenylenylene group, a pyrenylene group, a chrysenylene group, a pyrrolylene group, an imidazolylene group, a pyrazolylene group, a pyridinylene group, a pyrazinylene group, a pyrimidinylene group, an indolylene group, a quinolinylene group, an isoquinolinylene group, a phenanthridinylene group, a phenanthrolinylene group, a triazolylene group, a tetrazolylene group, and a triazinylene group.

In Formula 1, X may be selected from the group consisting of a phenylene group, a naphthylene group, a pyridinylene group, a pyrazinylene group, a pyrimidinylene group, a quinolinylene group, an isoquinolinylene group, and a triazinylene group.

In Formula 1, X may be selected from the group consisting of a phenylene group and a triazinylene group.

In Formula 1, $R_1$ may be selected from the group consisting of a $C_4$-$C_{20}$ alkyl group, a fluorine-substituted $C_4$-$C_{20}$ alkyl group, a $C_6$-$C_{20}$ aryl group, a fluorine-substituted $C_6$-$C_{20}$ aryl group, —NH($Q_1$), and —N($Q_1$)($Q_2$); and $Q_1$ and $Q_2$ may be each independently selected from the group consisting of a $C_4$-$C_{20}$ alkyl group, a fluorine-substituted $C_4$-$C_{20}$ alkyl group, a $C_6$-$C_{20}$ aryl group, and a fluorine-substituted $C_6$-$C_{20}$ aryl group.

In Formula 1, $R_1$ may be selected from the group consisting of —NH($Q_1$) and —N($Q_1$)($Q_2$); and $Q_1$ and $Q_2$ may be each independently selected from the group consisting of a $C_4$-$C_{20}$ alkyl group and a fluorine-substituted $C_4$-$C_{20}$ alkyl group.

In Formula 1, $R_1$ may be selected from the group consisting of —NH($Q_1$) and —N($Q_1$)($Q_2$); and $Q_1$ and $Q_2$ may be each independently selected from a fluorine-substituted $C_4$-$C_{20}$ alkyl group.

In Formula 1, a1 may be selected from 1 and 2.

In Formula 1, $R_2$ may be selected from the group consisting of —OH, —SH, —SO$_3$, —NH$_2$, —P(O)(OH)$_2$, —OP(O)(OH)$_2$, —O$_2$P(O)(OH), —(O)$_3$P(O), —Si(Q$_3$)(Q$_4$)(Q$_5$), —CO$_2$H, and an N(nitrogen)-containing $C_1$-$C_5$ heteroaryl group; and $Q_3$ and $Q_5$ may be each independently selected from the group consisting of hydrogen and a $C_1$-$C_{10}$ alkyl group.

In Formula 1, $R_2$ may be selected from the group consisting of —OH, —SH, —SO$_3$, —NH$_2$, —P(=O)(OH)$_2$, —OP(=O)(OH)$_2$, —O$_2$P(=O)(OH), —O$_3$P(=O), —Si(CH$_3$)$_3$, —Si(C$_2$H$_5$)$_3$, —CO$_2$H, a pyrrolyl group, an imidazolyl group, a pyrazolyl group, a thiazolyl group, a pyridinyl group, a pyrimidinyl group, a pyridazinyl group, a pyrrolidone group, a triazolyl group, a tetrazolyl group, and a triazinyl group.

In Formula 1, a2 may be selected from 1 and 2.

The bleed-out preventing agent may be represented by Formula 1A:

<Formula 1A>

In Formula 1A, $X_{11}$ to $X_{13}$ are each independently selected from a nitrogen atom (N) and CH;

$R_{11}$ and $R_{12}$ are each independently selected from the group consisting of hydrogen, a $C_1$-$C_{60}$ alkyl group, a fluorine-substituted $C_1$-$C_{60}$ alkyl group, a $C_6$-$C_{60}$ aryl group, and a fluorine-substituted $C_6$-$C_{60}$ aryl group; and $R_{21}$ and $R_{22}$ are each independently selected from functional groups including one or more heterogeneous elements that are selected from the group consisting of O, S, B, N, P, and Si.

In Formula 1A, $X_{11}$ to $X_{13}$ may be N.

In Formula 1A, $R_{11}$ and $R_{12}$ may be each independently selected from the group consisting of hydrogen and a fluorine-substituted $C_4$-$C_{20}$ alkyl group.

In Formula 1A, $R_{21}$ and $R_{22}$ may be each independently selected from the group consisting of —OH, —SH, —SO$_3$, —NH$_2$, —P(=O)(OH)$_2$, —OP(=O)(OH)$_2$, —O$_2$P(=O)(OH), —O$_3$P(=O), —Si(CH$_3$)$_3$, —Si(C$_2$H$_5$)$_3$, —CO$_2$H, a pyrrolyl group, an imidazolyl group, a pyrazolyl group, a thiazolyl group, a pyridinyl group, a pyrimidinyl group, a pyridazinyl group, a pyrrolidone group, a triazolyl group, a tetrazolyl group, and a triazinyl group.

According to one or more embodiments of the present invention, a composition for preventing bleed-out includes the above-described bleed-out preventing agent.

The composition for preventing bleed-out may not include a discoloration inhibitor.

According to one or more embodiments of the present invention, a method of preventing bleed-out includes treating with the above-described composition for preventing bleed-out.

The treating may include depositing the composition for preventing bleed-out on a wiring base.

The treating may include scattering or coating the composition for preventing bleed-out.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
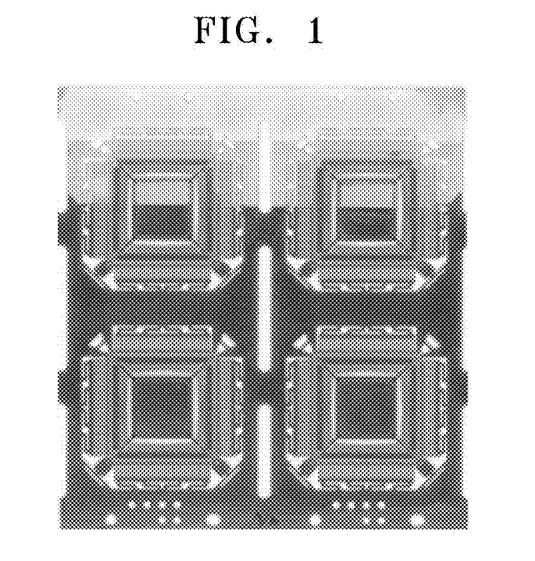
FIG. 1 is an image illustrating a result according to Evaluation Example 2 of Comparative Example 1.
Figure 2:
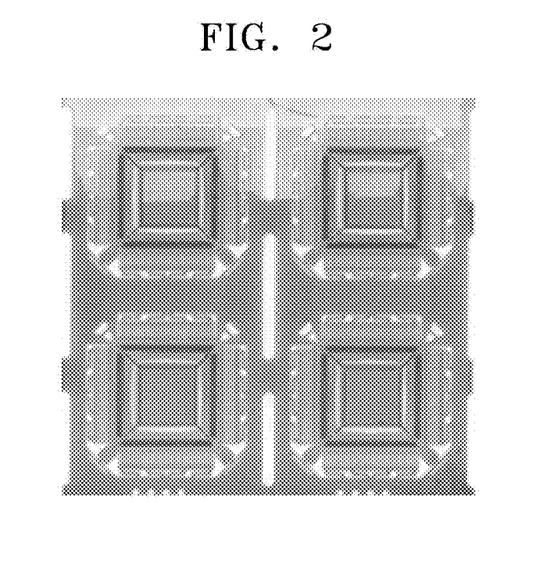
FIG. 2 is an image illustrating a result according to Evaluation Example 2 of Comparative Example 2.
Figure 3:
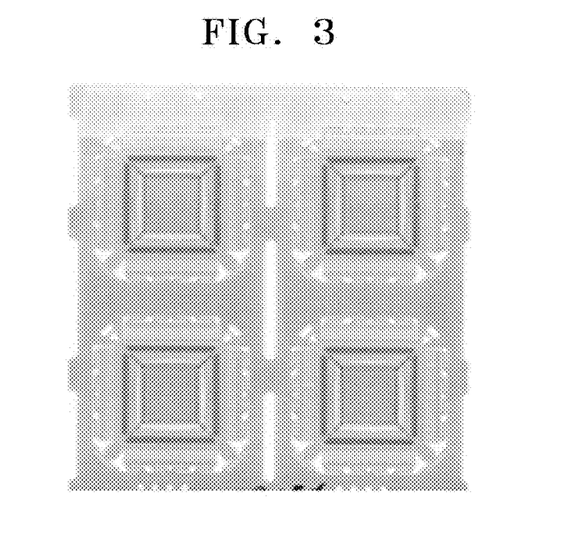
FIG. 3 is an image illustrating a result according to Evaluation Example 2 of Example 1.
Figure 4:
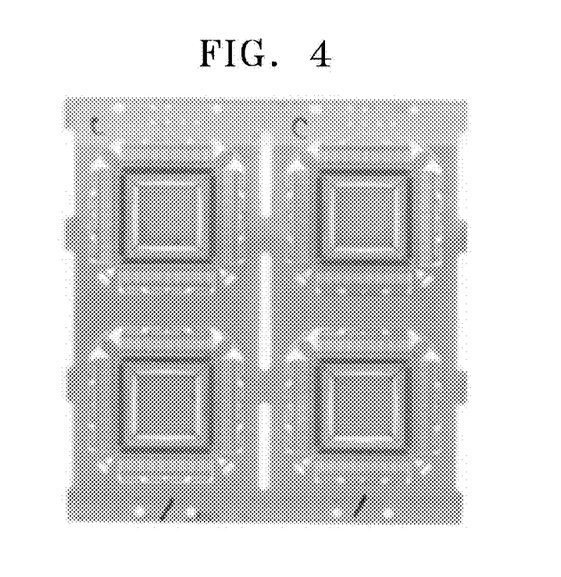
FIG. 4 is an image illustrating a result according to Evaluation Example 2 of Example 2.
Figure 5:
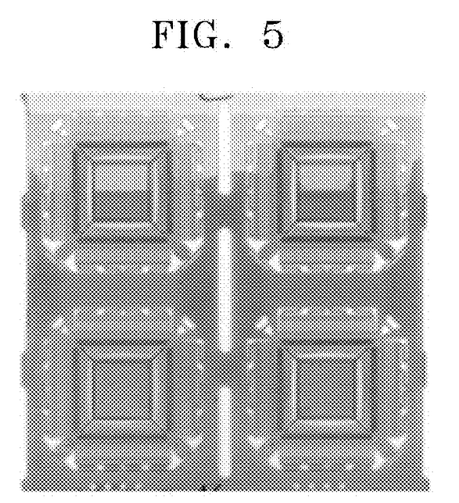
FIG. 5 is an image illustrating a result according to Evaluation Example 3 of Comparative Example 1.
Figure 6:
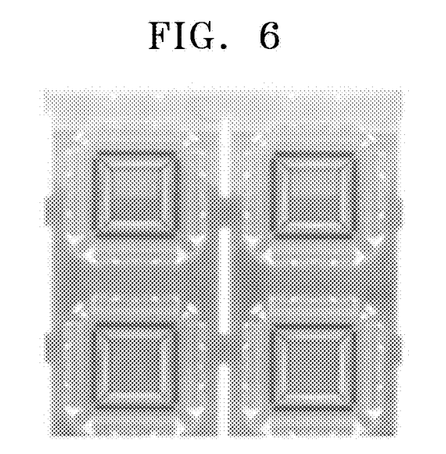
FIG. 6 is an image illustrating a result according to Evaluation Example 3 of Comparative Example 2.
Figure 7:
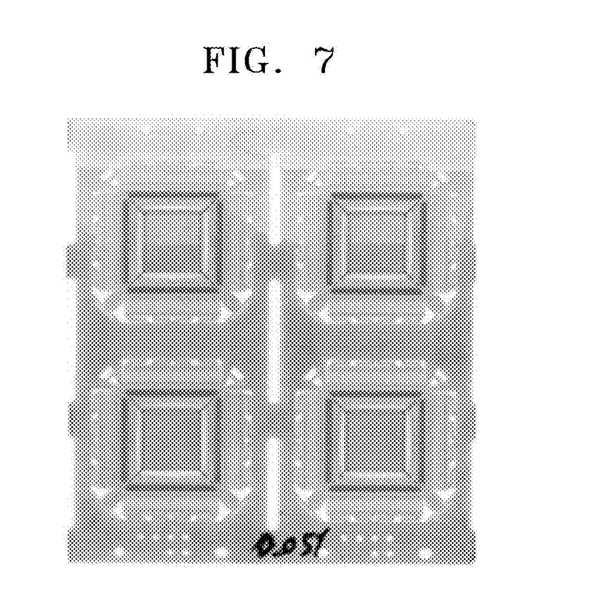
FIG. 7 is an image illustrating a result according to Evaluation Example 3 of Example 1.
Figure 8:
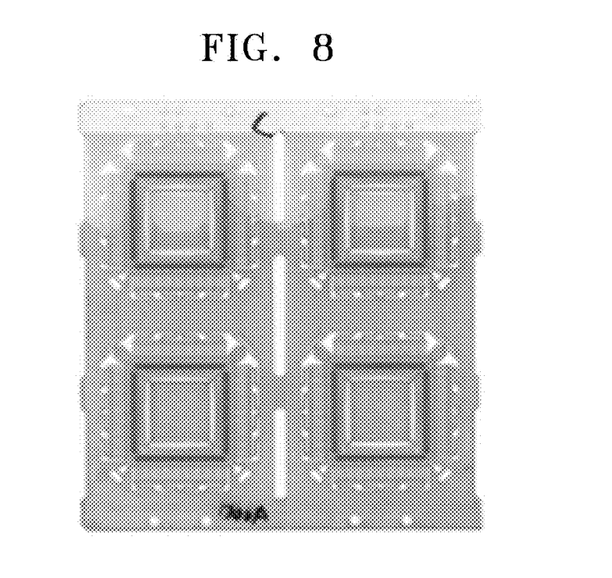
FIG. 8 is an image illustrating a result according to Evaluation Example 3 of Example 2.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description.

While the invention is amenable to various modifications and alternative forms, specific embodiments have been shown by way of example in the drawings and are described in detail below. Effects and features of the present invention, and implementation methods thereof will be clarified through following embodiments described with reference to the accompanying drawings. The present invention may, however, be embodied in different forms and should not be construed as limited to the embodiments set forth herein.

It will be further understood that the terms "comprises" and/or "comprising" used herein specify the presence of stated features or components, but do not preclude the presence or addition of one or more other features or components.

When a certain embodiment may be implemented differently, a specific process order may be performed differently from the described order. For example, two consecutively described processes may be performed substantially at the same time or performed in an order opposite to the described order.

As used herein, the term "and/or" includes any and all combinations of one or more of the associated listed items.

Hereinafter, a bleed-out preventing agent according to an embodiment of the present invention and a composition for preventing bleed-out including the same will be described in detail.

In the present specification, the expression "bleed-out preventing agent" denotes a compound having an effect of preventing the bleed-out of a die bonding resin.

In the present specification, the expression "die bonding resin" denotes all kinds of resins that are used for fixing a die pad and a semiconductor chip.

In the present specification, a "fluorine-substituted $C_1$-$C_{60}$ alkyl group" may be represented by —$C_{b1}H_{b2}F_{b3}$ (where b1 is selected from integers between 1 and 60, b2 is selected from integers between 0 and 120, b3 is selected from integers between 1 and 121, and b2+b3=2b1+1). The fluorine-substituted $C_1$-$C_{60}$ alkyl group may be a straight chain or a branched chain.

In the present specification, a "fluorine-substituted $C_4$-$C_{20}$ alkyl group" may be represented by —$C_{b1}H_{b2}F_{b3}$ (where b1 is selected from integers between 4 and 20, b2 is selected from integers between 0 and 40, b3 is selected from integers between 1 and 41, and b2+b3=2b1+1). The fluorine-substituted $C_4$-$C_{20}$ alkyl group may be any one selected from the group consisting of —$C_4F_9$, —$C_6F_{13}$, —$C_8F_{17}$, —$C_{10}F_{21}$, —(CH$_2$)$_2$(CF$_2$)$_4$F, —(CH$_2$)$_2$(CF$_2$)$_6$F, —(CH$_2$)$_2$(CF$_2$)$_8$F, and —(CH$_2$)$_2$(CF$_2$)$_{10}$F, but is not limited thereto. The fluorine-substituted $C_4$-$C_{20}$ alkyl group may be a straight chain or a branched chain.

According to an embodiment of the present invention, the bleed-out preventing agent may be represented by Formula 1 below:

<Formula 1>

In Formula 1, X may be selected from the group consisting of a $C_6$-$C_{60}$ arylene group and a $C_1$-$C_{60}$ heteroarylene group.

For example, in Formula 1, X may be selected from the group consisting of a phenylene group, a naphthylenylene group, a phenanthrenylene group, an anthracenylene group, a triphenylenylene group, a pyrenylene group, a chrysenylene group, a pyrrolylene group, an imidazolylene group, a pyrazolylene group, a pyridinylene group, a pyrazinylene group, a pyrimidinylene group, an indolylene group, a quinolinylene group, an isoquinolinylene group, a phenanthridinylene group, a phenanthrolinylene group, a triazolylene group, a tetrazolylene group, and a triazinylene group, but is not limited thereto.

As another example, in Formula 1, X may be selected from the group consisting of a phenylene group, a naphthylene group, a pyridinylene group, a pyrazinylene group, a pyrimidinylene group, a quinolinylene group, an isoquinolinylene group, and a triazinylene group, but is not limited thereto. As another example, in Formula 1, X may be selected from the group consisting of a phenylene group and a triazinylene group, but is not limited thereto. In Formula 1, $R_1$ may be selected from the group consisting of a $C_1$-$C_{60}$ alkyl group, a fluorine-substituted $C_1$-$C_{60}$ alkyl group, a $C_6$-$C_{60}$ aryl group, a fluorine-substituted $C_6$-$C_{60}$ aryl group, —NH($Q_1$), and —N($Q_1$)($Q_2$); and $Q_1$ and $Q_2$ may be each independently selected from the group consisting of a $C_1$-$C_{60}$ alkyl group, a fluorine-substituted $C_1$-$C_{60}$ alkyl group, a $C_6$-$C_{60}$ aryl group, and a fluorine-substituted $C_6$-$C_{60}$ aryl group.

For example, in Formula 1, $R_1$ may be selected from the group consisting of a $C_4$-$C_{20}$ alkyl group, a fluorine-substituted $C_4$-$C_{20}$ alkyl group, a $C_6$-$C_{20}$ aryl group, a fluorine-substituted $C_6$-$C_{20}$ aryl group, —NH($Q_1$), and —N($Q_1$)($Q_2$); and $Q_1$ and $Q_2$ may be each independently selected from the group consisting of a $C_4$-$C_{20}$ alkyl group, a fluorine-substituted $C_4$-$C_{20}$ alkyl group, a $C_6$-$C_{20}$ aryl group, and a fluorine-substituted $C_6$-$C_{20}$ aryl group, but is not limited thereto.

As another example, in Formula 1, $R_1$ may be selected from the group consisting of —NH($Q_1$) and —N($Q_1$)($Q_2$); and $Q_1$ and $Q_2$ may be each independently selected from the group consisting of a $C_4$-$C_{20}$ alkyl group and a fluorine-substituted $C_4$-$C_{20}$ alkyl group, but is not limited thereto.

As another example, in Formula 1, $R_1$ may be selected from the group consisting of —NH($Q_1$) and —N($Q_1$)($Q_2$); and $Q_1$ and $Q_2$ may be each independently selected from a fluorine-substituted $C_4$-$C_{20}$ alkyl group, but is not limited thereto.

In Formula 1, a1 denotes the number of $R_1$ that is substituted into X, and a1 may be selected from 1, 2, and 3. For example, in Formula 1, a1 may be selected from 1 and 2, but is not limited thereto. In a case where a1 is 2 or more, the plurality of $R_1$ may be the same or different from each other.

In Formula 1, $R_2$ may be selected from functional groups including one or more heterogeneous elements that are selected from the group consisting of oxygen (O), sulfur (S), boron (B), nitrogen (N), phosphorous (P), and silicon (Si).

For example, in Formula 1, $R_2$ may be selected from functional groups including one or more heterogeneous elements that are selected from the group consisting of O, S, N, P, and Si. Examples of the functional group may be a mercapto group, an amino group, an N-containing heterocyclic group, a phosphate ester group, and a carboxyl group.

As another example, in Formula 1, $R_2$ may be selected from the group consisting of —OH, —SH, —$SO_3$, —$NH_2$, —P(O)(OH)$_2$, —OP(O)(OH)$_2$, —$O_2$P(O)(OH), —(O)$_3$P(O), —Si($Q_3$)($Q_4$)($Q_5$), —$CO_2$H, and an N-containing $C_1$-$C_5$ heteroaryl group; and $Q_3$ and $Q_5$ may be each independently selected from the group consisting of hydrogen and a $C_1$-$C_{10}$ alkyl group, but is not limited thereto. As another example, in Formula 1, $R_2$ may be selected from the group consisting of —OH, —SH, —$SO_3$, —$NH_2$, —P(O)(OH)$_2$, —OP(=O)(OH)$_2$, —$O_2$P(=O)(OH), —$O_3$P(=O), —Si(CH$_3$)$_3$, —Si($C_2H_5$)$_3$, —$CO_2$H, a pyrrolyl group, an imidazolyl group, a pyrazolyl group, a thiazolyl group, a pyridinyl group, a pyrimidinyl group, a pyridazinyl group, a pyrrolidone group, a triazolyl group, a tetrazolyl group, and a triazinyl group, but is not limited thereto.

In Formula 1, a2 denotes the number of $R_2$ that is substituted into X, and may be selected from 1, 2, and 3. For example, in Formula 1, a2 may be selected from 1 and 2, but is not limited thereto. In a case where a2 is an integer of 2 or more, the plurality of $R_2$ may be the same or different from each other.

According to an embodiment of the present invention, the bleed-out preventing agent may be represented by Formula 1A below, but is not limited thereto.

<Formula 1A> where $X_{11}$ to $X_{13}$ may be each independently selected from a nitrogen atom (N) and CH.

For example, in Formula 1A, $X_{11}$ to $X_{13}$ may be N, but is not limited thereto.

In Formula 1A, $R_{11}$ and $R_{12}$ may be each independently selected from the group consisting of hydrogen, a $C_1$-$C_{60}$ alkyl group, a fluorine-substituted $C_1$-$C_{60}$ alkyl group, a $C_6$-$C_{60}$ aryl group, and a fluorine-substituted $C_6$-$C_{60}$ aryl group, but is not limited thereto.

For example, in Formula 1A, $R_{11}$ and $R_{12}$ may be each independently selected from the group consisting of hydrogen and a fluorine-substituted $C_4$-$C_{20}$ alkyl group, but is not limited thereto.

In Formula 1A, $R_{21}$ and $R_{22}$ may be each independently selected from functional groups including one or more heterogeneous elements that are selected from the group consisting of O, S, B, N, P, and Si.

For example, in Formula 1A, $R_{21}$ and $R_{22}$ may be each independently selected from the group consisting of —OH, —SH, —$SO_3$, —$NH_2$, —P(=O)(OH)$_2$, —OP(=O)(OH)$_2$, —$O_2$P(=O)(OH), —$O_3$P(=O), —Si(CH$_3$)$_3$, —Si($C_2H_5$)$_3$, —$CO_2$H, a pyrrolyl group, an imidazolyl group, a pyrazolyl group, a thiazolyl group, a pyridinyl group, a pyrimidinyl group, a pyridazinyl group, a pyrrolidone group, a triazolyl group, a tetrazolyl group, and a triazinyl group, but is not limited thereto.

According to another embodiment of the present invention, the bleed-out preventing agent may be selected from Compound 1 and Compound 2 below, but is not limited thereto.

The bleed-out preventing agent represented by Compound 1 may prevent discoloration of a die pad even if the die pad is not treated with a separate discoloration inhibitor.

According to another embodiment of the present invention, a composition for preventing bleed-out includes the bleed-out preventing agent represented by Compound 1.

The composition for preventing bleed-out may not include a separate discoloration inhibitor. Since the bleed-out preventing agent represented by Compound 1 may simultaneously prevent bleed-out and discoloration, the discoloration of a metal surface of a board may be prevented even if the bleed-out preventing agent does not include a separate discoloration inhibitor.

Since the composition for preventing bleed-out does not include a separate discoloration inhibitor, two or more different organic compounds are not competitively adsorbed on the metal surface of the board. For example, with respect to a composition including a discoloration inhibitor in addition to a bleed-out preventing agent, the bleed-out preventing agent and the discoloration inhibitor may be competitively adsorbed on the metal surface of the board. In contrast, with respect to the composition for preventing bleed-out, only the bleed-out preventing agent may be adsorbed on the metal surface of the board without any competition with other compounds. Therefore, the composition for preventing bleed-out, a trade-off between bleed-out prevention and discoloration prevention may not occur and two functions may be simultaneously improved.

Since the composition for preventing bleed-out has a simple composition, consistent quality management of the composition for preventing bleed-out may be facilitated.

The composition for preventing bleed-out may include a solvent. A concentration of the bleed-out preventing agent in the composition for preventing bleed-out may be in a range of about 0.001 wt % to about 0.10 wt %. For example, the concentration of the bleed-out preventing agent in the composition for preventing bleed-out may be in a range of about 0.005 wt % to about 0.05 wt %, but is not limited thereto. When the amount of the bleed-out preventing agent is within the above range, the bleed-out preventing agent may sufficiently exhibit a bleed-out prevention effect.

The solvent may be water and/or an organic solvent. The organic solvent may have miscibility with water, and in a case where the bleed-out preventing agent is not dissolved in water, it may be sufficient to include the organic solvent in an amount capable of dissolving the bleed-out preventing agent. For example, the organic solvent may be methanol, ethanol, isopropanol, t-butanol, acetone, methylethylketone, or tetrahydrofuran, but is not limited thereto.

The composition for preventing bleed-out may further include a pH buffer. The pH buffer may be a phosphoric acid-based, boric acid-based, or organic acid-based pH buffer. The pH buffer may be included in an amount of about 0.1 g/L to about 200 g/L based on a total volume of the composition. For example, the pH buffer may be included in an amount of about 1 g/L to about 50 g/L based on the total volume of the composition, but is not limited thereto. When the amount of the pH buffer is within the above range, a buffering effect may be sufficiently obtained.

The composition for preventing bleed-out may further include a complexing agent. The complexing agent may be an amine-based, amino carboxylic acid-based, or carboxylic acid-based complexing agent. The complexing agent may be included in an amount of about 0.1 g/L to about 200 g/L based on the total volume of the composition. For example, the complexing agent may be included in an amount of about 1 g/L to about 50 g/L based on the total volume of the composition, but is not limited thereto. When the amount of the complexing agent is within the above range, an effect of complexing metal ions may be sufficiently obtained.

A pH value of the composition for preventing bleed-out is not particularly limited. However, in general, the pH value of the composition for preventing bleed-out may be in a range of about 1 to about 14. For example, the pH value of the composition for preventing bleed-out may be in a range of about 2 to about 12, but is not limited thereto. When the pH value is outside the above range, damage to the die pad may be large and the bleed-out prevention effect may be low.

The composition for preventing bleed-out may further include a surfactant. The surfactant may be an anionic-based, cationic-based, and non-ionic-based surfactant. The surfactant may be included in an amount of about 0.1 g/L to about 100 g/L based on the total volume of the composition. For example, the surfactant may be included in an amount of about 1 g/L to about 50 g/L based on the total volume of the composition, but is not limited thereto. When the amount of the surfactant is within the above range, effects of dispersing the bleed-out preventing agent in water and improving the wettability of the metal surface of the board with respect to the composition for preventing bleed-out may be sufficiently obtained.

A die pad may be treated with the composition for preventing bleed-out to prevent bleed-out. The composition for preventing bleed-out may be used by a method of depositing the composition for preventing bleed-out on the die pad, but is not limited thereto. The composition for preventing bleed-out may be used by a method of showering, spraying, scattering, or coating the composition for preventing bleed-out on the metal surface of the board, but is not limited thereto.

A treatment temperature of the composition for preventing bleed-out is not particularly limited so long as the treatment temperature is in a range in which the treatment may be performed with the composition for preventing bleed-out in a liquid state. For example, the treatment temperature of the composition for preventing bleed-out may be in a range of about 5° C. to about 90° C., but is not limited thereto. As another example, the treatment temperature of the composition for preventing bleed-out may be in a range of about 10° C. to about 60° C., but is not limited thereto. The treatment temperature of the composition for preventing bleed-out may be in a range of about 10° C. to about 60° C. When the treatment temperature of the com- position for preventing bleed-out is within the above range, workability may be high while the bleed-out prevention effect may be sufficiently obtained.

A treatment time of the composition for preventing bleed-out may be in a range of about 0.1 seconds to about 300 seconds. For example, the treatment time of the composition for preventing bleed-out may be in a range of about 1 second to about 120 seconds, but is not limited thereto. When the treatment time of the composition for preventing bleed-out is within the above range, reproducibility of the treatment work may be high while the bleed-out prevention effect may be sufficiently obtained.

Hereinafter, the present invention will be described in detail, according to specific examples. However, the following examples are merely presented to exemplify the present invention, and it is obvious to those skilled in the art that the scope of the present invention is not limited thereto.

EXAMPLE 1

Silver (Ag) plating was performed on an entire surface of a lead frame base formed of a copper alloy (Cu: 97%, impurity elements such as iron (Fe), zinc (Zn), and P: 3%). Next, the lead frame was deposited with a composition for preventing bleed-out in which about 0.05 wt % of a bleed-out preventing agent of the following Formula was dissolved in isopropanol (IPA).

EXAMPLE 2

Ag plating was performed on an entire surface of a lead frame base formed of a copper alloy (Cu: 97%, impurity elements such as Fe, Zn, and P: 3%). Next, the lead frame was deposited with a composition for preventing bleed-out in which about 0.05 wt % of a bleed-out preventing agent of the following Formula was dissolved in IPA.

COMPARATIVE EXAMPLE 1

An experiment was conducted in the same manner as in Example 1 except that a treatment with a composition for preventing bleed-out was not performed.

COMPARATIVE EXAMPLE 2

An experiment was conducted in the same manner as in Example 1 except that a composition including about 0.05 wt % of hexadecanethiol (HDT, $C_{16}H_{34}S$), about 0.01 wt % of benzotriazole (BTA, $C_6H_5N_3$), about 10 wt % of IPA, about 0.05 wt % of Tween 80 surfactant (T80), and water as a remainder was used as a composition for preventing bleed-out.

EVALUATION EXAMPLE 1

Bleed-Out Prevention Evaluation

The lead frames of Examples 1 and 2 and Comparative Examples 1 and 2 were dotted with a commercial die bonding resin (Ablebond 8340A, Ablestik) using a syringe. Next, the lead frames were left standing for about 1 hour at room temperature in an atmospheric pressure, and then cured at about 175° C. for about 1 hour in a curing oven. Thereafter, maximum bleed-out lengths were measured by observing portions of the lead frames dotted with the die bonding resin with an optical microscope (×100). The results thereof are presented in Table 1.

EVALUATION EXAMPLE 2

Discoloration Prevention Evaluation (1)—No Heat Treatment Condition

The lead frames of Examples 1 and 2 and Comparative Examples 1 and 2 were cut to an appropriate size and were left standing for about 30 minutes at about 25° C. in a closed chamber including about 20 ml of a 5% ammonium sulfide (($NH_4)_2S$) aqueous solution. Next, surface brightness of the lead frames before/after an ammonium sulfide exposure treatment was measured with a microscopic area color meter or gloss meter (VSR-400, Nippon Denshoku Industries, Co., Ltd.), and the results thereof are presented in Table 1.

EVALUATION EXAMPLE 3

Discoloration Prevention Evaluation (2)—Heat Treatment Condition

In order to indirectly evaluate a discoloration prevention effect after a heat treatment of a lead frame subjected to a bleed-out prevention treatment in a semiconductor assembly process (die bonding, wire bonding, and epoxy molding compound (EMC) molding), the lead frames of Examples 1 and 2 and Comparative Examples 1 and 2 were cut to an appropriate size and then heat treated in an oven at about 175° C. for about 5 hours. Next, the lead frames were left standing for about 30 minutes at about 25° C. in a closed chamber including about 20 ml of a 5% $(NH_4)_2S$ aqueous solution.

Thereafter, surface brightness of the lead frames before/after an ammonium sulfide exposure treatment was measured with a microscopic area color meter or gloss meter (VSR-400, Nippon Denshoku Industries, Co., Ltd.), and the results thereof are presented in Table 1.

TABLE 1

| Category | | Comparative Example 1 | Comparative Example 2 | Example 1 | Example 2 |
|---|---|---|---|---|---|
| Anti-EBO chemical composition | | No treatment | HDT: 0.05 wt % BTA: 0.01 wt % IPA: 10 wt % Tween 80: 0.05 wt % $H_2O$: remainder | 0.05 wt % IPA solution | 0.05 wt % IPA solution |
| Treatment condition | Temperature (° C.) | 25 | 25 | 25 | 25 |
| | Time (s) | 10 | 10 | 10 | 10 |
| EBO (mm) | | >1.000 | 0 | 0.025 | 0 |
| Discoloration (no heat treatment) | ΔBR* | >0.4 | 0.28 | 0.05 | 0.10 |
| Discoloration (heat treatment) | ΔBR | >0.3 | 0.15 | 0.12 | 0.14 |

*ΔBR was measured as a difference between the brightness measurement values before/after the $(NH_4)_2S$ exposure. That is, ΔBR is a value of (BR after the $(NH_4)_2S$ exposure − BR before the $(NH_4)_2S$ exposure). The ΔBR value increases as discoloration due to sulfur is more severe.

Referring to Table 1, it may be understood that the composition for preventing bleed-out including the bleed-out preventing agent represented by Formula 1 may simultaneously prevent bleed-out and discoloration. Specifically, it may be confirmed that the composition for preventing bleed-out may prevent oxidation discoloration of an Ag-plated portion of the lead frame due to sulfur, or oxidation discoloration or high-temperature oxidation of a non-plated portion of copper (Cu) of the lead frame.

As described above, according to the one or more of the above embodiments of the present invention, bleed-out preventing agents that may simultaneously realize bleed-out prevention and discoloration prevention, compositions for preventing bleed-out including the same, and methods of preventing bleed-out may be provided.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments of the present invention have been described with reference to the figures, it will be understood by those of ordinary skill in the art that various changes in form and details may be made therein without departing from the spirit and scope of the present invention as defined by the following claims.

What is claimed is:

1. A compound represented by the following formula:

2. A composition for preventing bleed-out comprising the compound of claim 1 and at least one selected from the group consisting of a solvent, a pH buffer and a surfactant.

3. The composition for preventing bleed-out of claim 2, not comprising a discoloration inhibitor.

4. A method of preventing bleed-out comprising treating with the composition for preventing bleed-out of claim 2.

5. The method of claim 4, wherein the treating comprises depositing the composition for preventing bleed-out on a wiring base.

6. The method of claim 4, wherein the treating comprises scattering or coating the composition for preventing bleed-out.

* * * * *